United States Patent [19]
Yale et al.

[11] 4,003,905
[45] Jan. 18, 1977

[54] DIELS-ALDER ADDUCTS OF BENZDIAZEPINES

[75] Inventors: Harry L. Yale, New Brunswick; James A. Bristol, Boonton, both of N.J.

[73] Assignee: E. R. Squibb & Sons, Inc., Princeton, N.J.

[22] Filed: Dec. 11, 1974

[21] Appl. No.: 531,512

[52] U.S. Cl. .......................... 260/293.55; 424/267
[51] Int. Cl.² ............. C07D 471/18; C07D 498/18; C07D 513/18
[58] Field of Search ............... 260/293.55

[56] References Cited
UNITED STATES PATENTS

| | | | |
|---|---|---|---|
| 3,639,408 | 2/1972 | Nagata et al. | 260/293.53 |
| 3,763,183 | 10/1973 | Carabateas | 260/326.3 |
| 3,868,372 | 2/1975 | Hardtmenn | 260/251 A |

*Primary Examiner*—G. Thomas Todd
*Attorney, Agent, or Firm*—Lawrence S. Levinson; Merle J. Smith; Donald J. Barrack

[57] ABSTRACT

Compounds having the structure

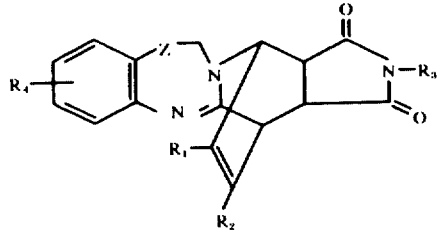

and pharmaceutically acceptable salts thereof, wherein Z is oxygen, sulfur or methylene; $R_1$ is hydrogen, halogen, alkyl, aryl or arylalkyl; $R_2$ is hydrogen, alkyl, aryl, or arylalkyl; $R_3$ is hydrogen, alkyl, aryl or arylalkyl; and $R_4$ is hydrogen, halogen, alkyl, phenyl, dialkylamidosulfonyl or trifluoromethyl, have useful central nervous system activity.

7 Claims, No Drawings

DIELS-ALDER ADDUCTS OF BENZDIAZEPINES

SUMMARY OF THE INVENTION

Compounds having the structure

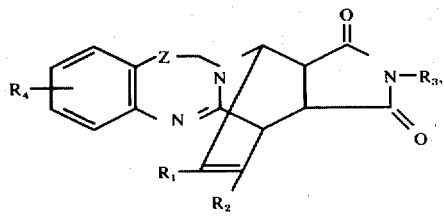

and the pharmaceutically acceptable salts thereof, have useful pharmacological activity. In formula I, and throughout the specification, the symbols are as defined below:

Z is oxygen, sulfur or methylene;
$R_1$ is hydrogen, halogen, alkyl, aryl or arylalkyl;
$R_2$ is hydrogen, alkyl, aryl or arylalkyl;
$R_3$ is hydrogen, alkyl, aryl or arylalkyl; and
$R_4$ is hydrogen, halogen, alkyl, phenyl, dialkylamidosulfonyl or trifluoromethyl;
with the proviso that when Z is oxygen or sulfur, and $R_4$ is phenyl or dialkylamidosulfonyl, $R_4$ must be para to the oxygen or sulfur atom.

The term alkyl, as used throughout the specification, refers to straight or branched chain alkyl groups having 1 to 4 carbon atoms. Methyl is the preferred alkyl group.

The term aryl, as used throughout the specification, refers to phenyl or phenyl substituted with halogen, alkyl or alkoxy. Phenyl is the preferred aryl group.

The term halogen, as used throughout the specification, refers to chlorine, fluorine and bromine. Chlorine and bromine are the preferred halogens.

The term alkoxy, as used throughout the specification, refers to groups having the formula Y—O— wherein Y is alkyl as defined above. Methoxy is the preferred alkoxy group.

DETAILED DESCRIPTION OF THE INVENTION

The compounds of this invention have useful central nervous system stimulant activity in mammalian species, such as rats, dogs, etc., and can be used in the same manner as dextroamphetamine for the treatment of drowsiness or for the supression of appetite.

The compounds of this invention can be administered in a daily dose of from about 25 milligrams/70 kilograms to 2 grams/70 kilograms, preferably from about 25 milligrams/70 kilograms to 1 gram/70 kilograms. The compounds can be administered orally or parenterally in the form of tablets, capsules, elixirs, injectables or the like by incorporating the appropriate dosage of the compound with carriers according to accepted pharmaceutical practice.

The compounds of formula I can be prepared from maleimides having the structure

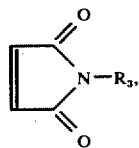

and from tricyclic compounds having the structure

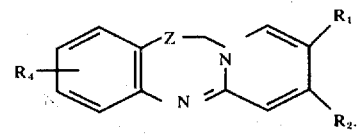

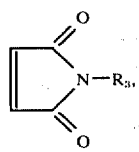

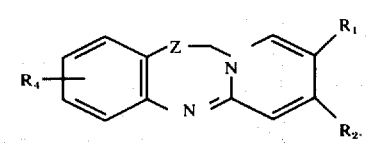

The N-maleimides of formula II are well known in the art and are readily obtainable by reaction of maleic anhydride and an amine having the formula $R_3$—$NH_2$. The compounds of formula III are known: see, U.S. Pat. No. 3,825,549, issued July 23, 1974; U.S. Pat. application, Ser. No. 347,938, filed Apr. 4, 1973, and now U.S. Pat. No. 3,857,850, issued Dec. 31, 1974; and U.S. Patent application, Ser. No. 347,939, filed Apr. 4, 1973, and now U.S. Pat. No. 3,856,801, issued Dec. 24, 1974.

The reaction of a tricyclic compound of formula III with an N-substituted maleimide of formula II can be carried out in an organic solvent at elevated temperatures. While the choice of solvent and reaction conditions is not critical, the reaction will most preferably be run in an aromatic hydrocarbon solvent, such as xylene, under reflux conditions.

The compounds of formula I can be converted into pharmaceutically acceptable acid addition salts using procedures well known in the art. Illustrative acid addition salts are the hydrohalides, especially the hydrochloride and hydrobromide which are preferred, sulfate, nitrate, phosphate, tartrate, maleate, fumarate, citrate, succinate, methanesulfonate, toluenesulfonate, benzenesulfonate and the like.

The compounds of formula I wherein $R_1$ and $R_2$ are hydrogen are preferred.

The compounds of formula I wherein $R_1$, $R_2$ and $R_4$ are hydrogen are preferred.

The following examples are specific embodiments of this invention.

EXAMPLE 1

3a,4,13,13a-Tetrahydro-2-methyl-4,13-etheno-1H,6H-pyrrolo[3′,4′:4,5]pyrido[1,2-c][1,3,5]benzothiadiazepine-1,3(2H)-dione A solution of 6H-pyrido[1,2-c][1,3,5]benzothiadiazepine (0.8 g) and N-methylmaleimide (0.6 g) in 30 ml of xylene is heated under reflux with stirring for 16 hours. The reaction mixture is allowed to cool and 1.03 g of solid crude product is collected and washed with xylene. The crude material is recrystallized from 200 ml of toluene to give 0.6 g of the title compound, melting point 285°–287° C, dec.

EXAMPLE 2

3a,4,10,11,13,13a-Hexahydro-2-methyl-4,13-etheno-1H-pyrrolo[3',4':4,5]pyrido[2,1-b][1,3]benzodiazepine-1,3(2H)-dione A solution of 11,12-dihydropyrido[2,1-b][1,3]benzodiazepine (1.96 g) and N-methylmaleimide (1.68 g) in 50 ml of xylene is heated under reflux conditions for 23 hours. The reaction mixture is allowed to cool to room temperature and then placed in a refrigerator for about 16 hours. The product is isolated and dried to give 3.07 g of material. Recrystallization of the material from 50 ml of toluene gives 2.04 g of the title compound, which after drying in vacuo at 110° C for 6 hours, has a melting point of 215°—217° C.

EXAMPLE 3

10-Chloro-3a,4,13,13a-tetrahydro-2-methyl-4,13-etheno-1H,6H-pyrrolo[3',4':4,5]pyrido[1,2-c][1,3,5]-benzoxadiazepine-1,3(2H)-dione A solution of 2-chloro-6H-pyrido[1,2-c][1,3,5]benzoxadiazepine (0.58 g) and N-methylmaleimide (0.41 g) in 30 ml of xylene is heated under reflux conditions for 6 days. The solution is filtered while still hot and allowed to cool to room temperature. The crystalline material that separates is collected, washed with xylene and dried to give 0.6 g of the title compound, sintering at 240° C and having a melting point 250°–251° C.

EXAMPLE 4

3a,4,13,13a-Tetrahydro-2-phenyl-4,13-etheno-1H,6H-pyrrolo[3',4':4,5]pyrido[1,2-a][1,3,5]benzoxadiazepine-1,3(2H)-dione A mixture of 6H-pyrido[1,2-c][1,3,5]benzoxadiazepine (1.98 g) and N-phenylmaleimide (2.07 g) in 80 ml of xylene is heated under reflux conditions for 21 hours. After cooling to room temperature, the mixture is allowed to stand in a refrigerator for about 16 hours. The crude product is then collected and recrystallized from 250 ml of toluene. The material is filtered, suspended in hexane and filtered again. Drying in vacuo at 110° C for 6 hours gives 1.56 g of the title compound, melting point 243°–244° C.

EXAMPLE 5

3a,4,13,13a-Tetrahydro-2-methyl-4,13-etheno-1H,6H-pyrrolo[3',4':4,5]pyrido[1,2-c][1,3,5]benzoxadiazepine-1,3(2H)-dione A mixture of 6H-pyrido[1,2-c][1,3,5]benzoxadiazepine (1.98 g) and N-methylmaleimide (1.68 g) in 50 ml of xylene is heated under reflux conditions for 23 hours. The reaction mixture is allowed to cool to room temperature and then allowed to stand in a refrigerator for 5 hours. The crude product is collected, washed with xylene and dried in vacuo for about 16 hours at room temperature and for 6 hours at 110° C to give 2.43 g of the title compound, melting point 252°–253° C.

EXAMPLES 6 to 13

Following the procedure of Example 1, but substituting the benzothiadiazepine listed in column I for 6H-pyrido[1,2-c][1,3,5]benzothiadiazepine and the N-substituted maleimide listed in column II for N-methylmaleimide, the compound listed in column III is obtained.

-continued
| | | |
|---|---|---|
| 10 | 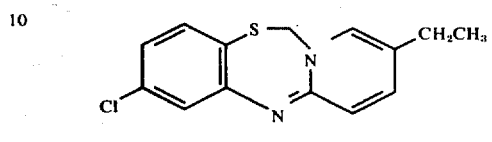 | 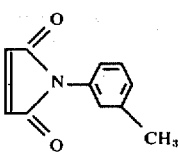 |
| 11 | 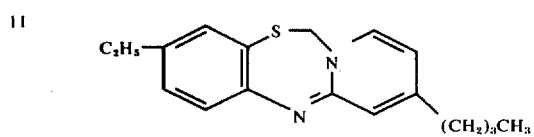 | 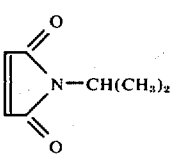 |
| 12 | 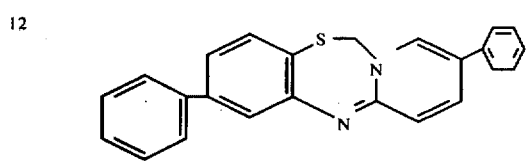 | 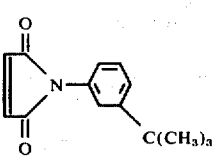 |
| 13 | 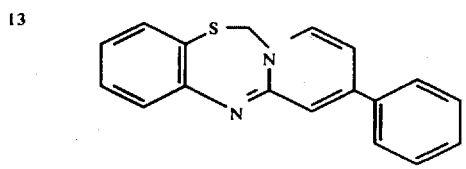 | 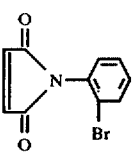 |
| Example | Column III |
|---|---|
| 6 | 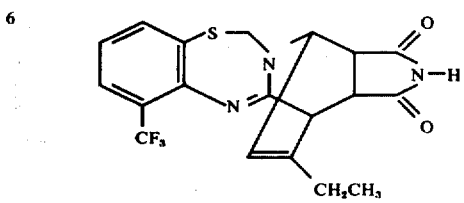 |
| 7 | 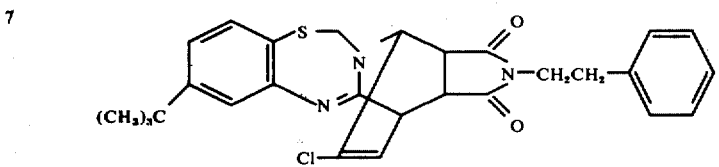 |
| 8 | 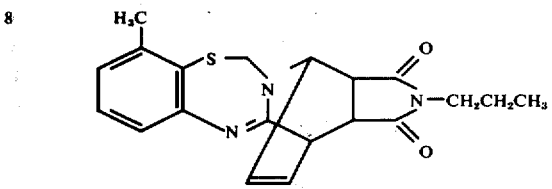 |
| 9 | 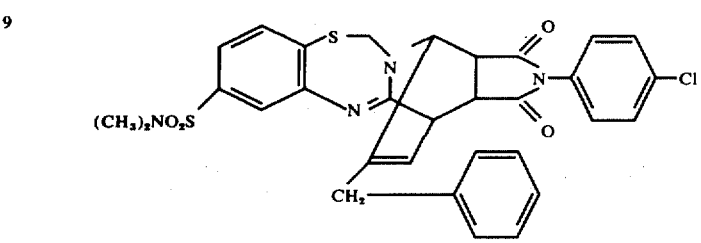 |

-continued
10 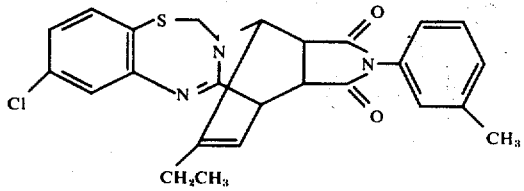
11 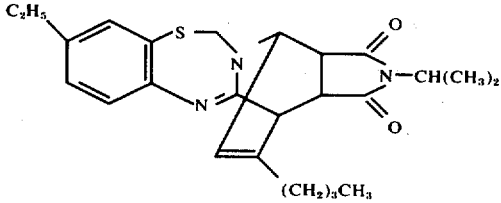
12 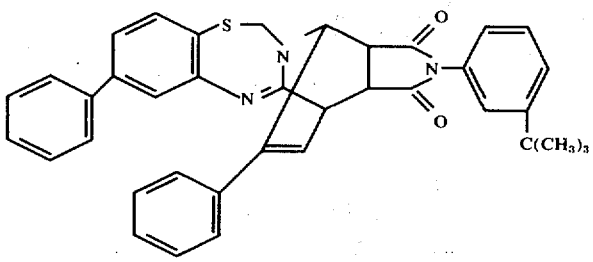
13 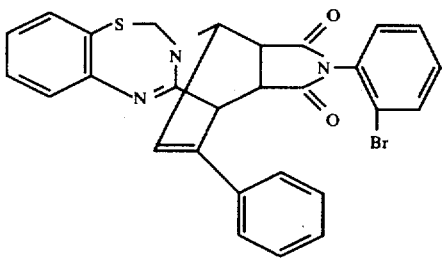
EXAMPLES 14 – 20
Following the procedure of Example 2, but substituting the benzodiazepine listed in column I for 11,12-dihydro-pyrido[2,1-b][1,3]benzodiazepine and the N-substituted maleimide for N-methylmaleimide listed in column II, the compound listed in column III is obtained.

-continued
| | | |
|---|---|---|
| 17 | 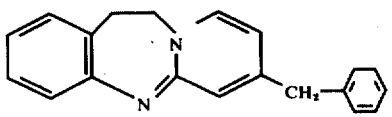 | 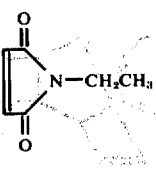 |
| 18 | 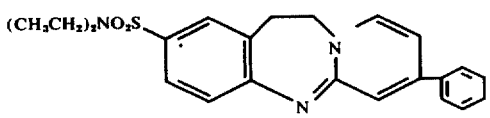 | 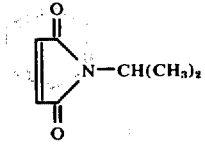 |
| 19 | 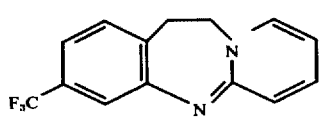 | 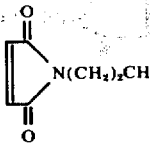 |
| 20 | 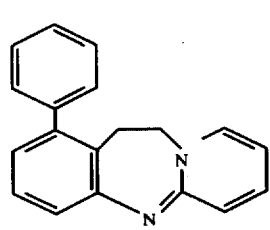 | 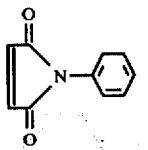 |
Example  Column III
| | |
|---|---|
| 14 | 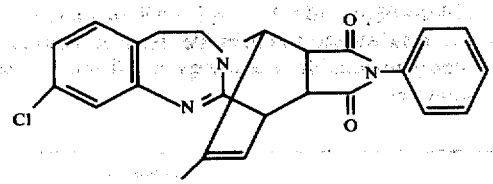 |
| 15 | 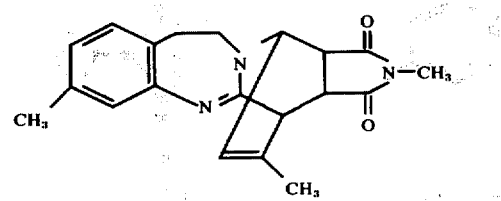 |
| 16 | 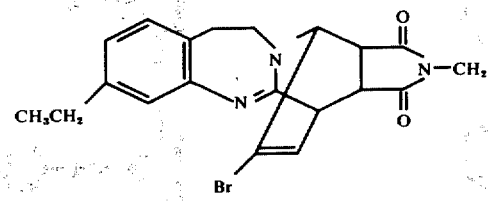 |
| 17 | 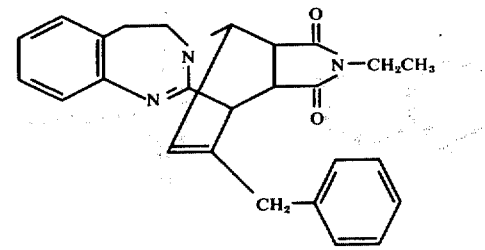 |

-continued
18 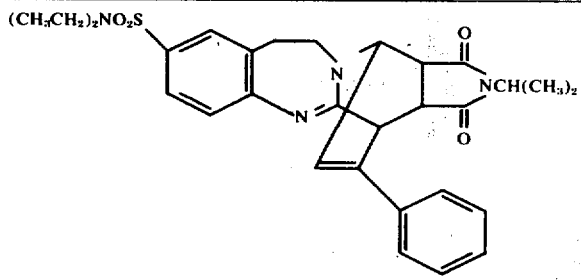
19 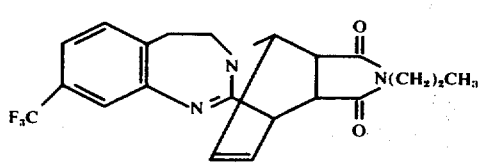
20 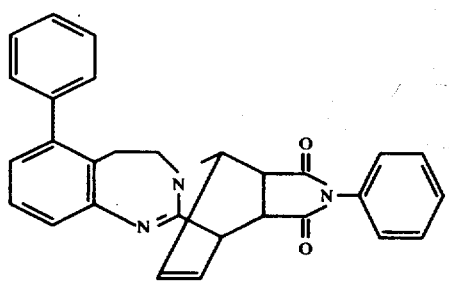
EXAMPLES 21 — 29
Following the procedure of Example 3, but substituting the benzoxadiazepine listed in column I for 2-chloro-6H-pyrido[1,2-c][1,3,5]benzoxadiazepine and the n-substituted maleimide listed in column II for N-methylmaleimide, the compound listed in column III is obtained.
| Example | Column I | Column II |
|---------|----------|-----------|
| 21 | | |
| 22 | | |
| 23 | | |
| 24 | | |

-continued
| | | |
|---|---|---|
| 25 | 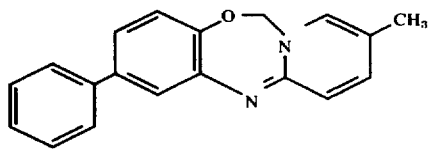 | 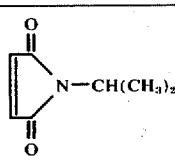 |
| 26 | 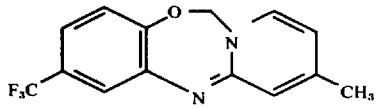 | 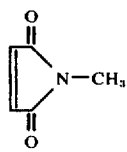 |
| 27 | 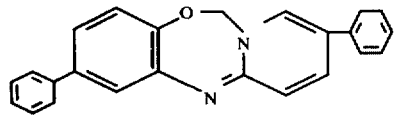 | 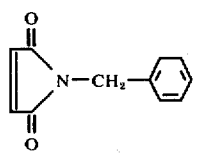 |
| 28 | 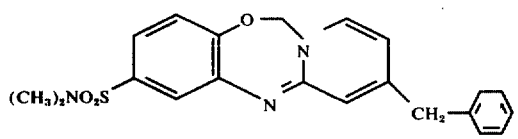 | 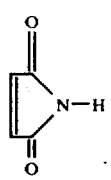 |
| 29 | 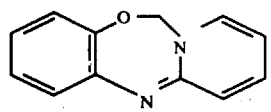 | 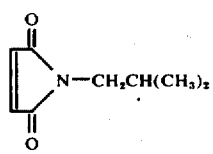 |
| Example | Column III |
|---|---|
| 21 | 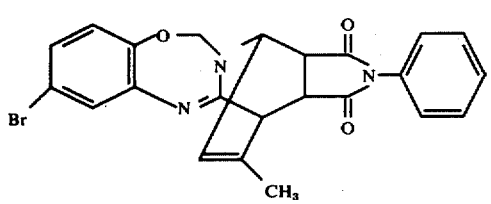 |
| 22 | 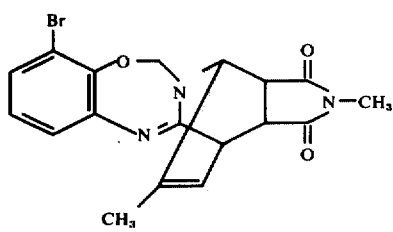 |
| 23 | 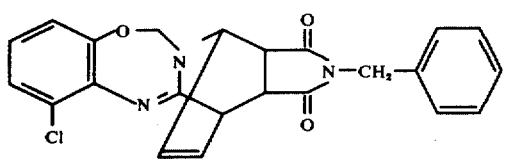 |
| 24 | 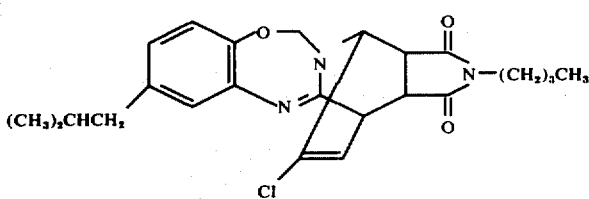 |

-continued

25
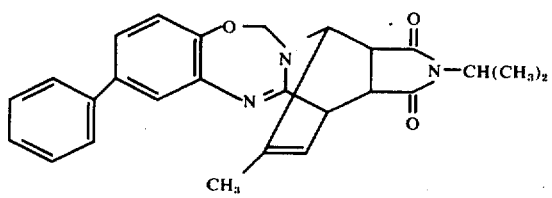

26
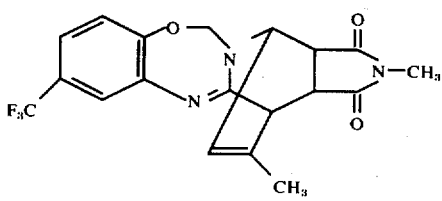

27
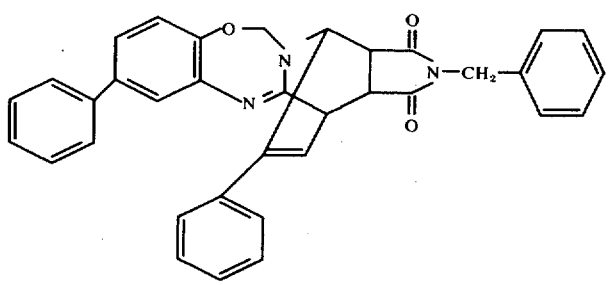

28
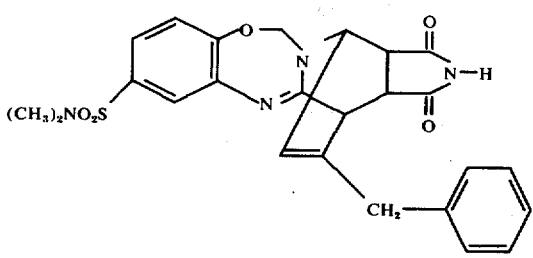

29
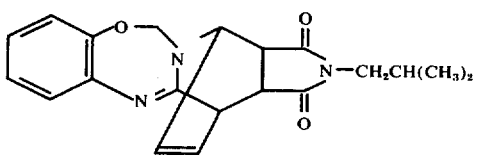

EXAMPLE 30

10-Chloro-3a,4,13,13a-tetrahydro-2-methyl-1H,6H-pyrrolo[3',4':4,5]pyrido[1,2-c][1,3,5]benzoxadiazepine-1,3(2H)dione, hydrochloride To 3.40 g of 10-chloro-3a,4,13,13a-tetrahydro-2-methyl-1H,6H-pyrrolo[3',4':4,5]pyrido[1,2-c][1,3,5]benzoxadiazepine-1,3(2H)dione in 25 ml of dry chloroform is added, dropwise, and with external wet ice cooling, 10.0 ml of a 1.05 N ethereal hydrogen chloride solution to obtain the title compound.

What is claimed is:
1. A compound having the structure

50
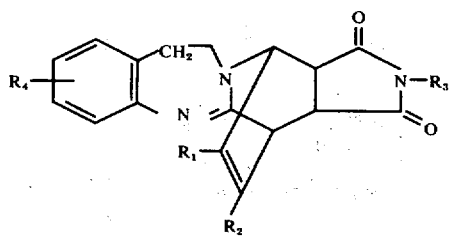

wherein $R_1$ is hydrogen, halogen, alkyl, aryl or arylalkyl; $R_2$ is hydrogen, alkyl, aryl or arylalkyl; $R_3$ is hydrogen, alkyl, aryl or arylalkyl; and $R_4$ is hydrogen, halogen, alkyl, phenyl, dialkylamidosulfonyl or trifluoromethyl; and wherein alkyl and alkoxy refer to groups having 1 to 4 carbon atoms and aryl refers to phenyl or phenyl substituted with halogen, alkyl or alkoxy.

2. A compound in accordance with claim 1 wherein $R_1$ and $R_2$ are hydrogen.

3. A compound in accordance with claim 1 wherein $R_3$ is hydrogen.

4. A compound in accordance with claim 1 wherein $R_3$ is alkyl.

5. A compound in accordance with claim 1 wherein $R_3$ is aryl.

6. A compound in accordance with claim 1 wherein $R_3$ is arylalkyl.

7. The compound in accordance with claim 1 having the name 3a,4,10,11,13,13a-hexahydro-2-methyl-4,13-etheno-1H-pyrrolo[3',4':4,5]pyrido[2,1-b][1,3]benzodiazepine-1,3(2H)-dione.

* * * * *